United States Patent [19]

Tabor et al.

[11] 4,291,020

[45] Sep. 22, 1981

[54] INACTIVATION OF NON-A, NON-B HEPATITIS AGENT

[75] Inventors: Edward Tabor, Rockville; Robert J. Gerety, Potomac, both of Md.

[73] Assignee: The United States of America as represented by the Secretary of Health & Human Services, Washington, D.C.

[21] Appl. No.: 150,320

[22] Filed: May 16, 1980

[51] Int. Cl.³ ............................................. A61K 39/29
[52] U.S. Cl. ...................................... 424/89; 435/238
[58] Field of Search ........................... 424/89; 435/238

[56] References Cited

PUBLICATIONS

Wester Mann et al. Zentralec. Bakteriol. Parasitenk D. Infeckionskr. Hyg. ABT. I: Reihe A, 1978 240(2):143-151, Studies on the Effect of Formaldehyde on the Immunological Reactivity and Morphology of Hepatitis B-Antigens.

Tabor et al., Lancet, Mar. 4, 1978, pp. 463-466 Transmission of Non-A, Non-B Hepatitis from Man to Chimpanzee.

Tabor et al. Acute Non-A Non-B Hepatitis Prolonged Presence of the Infectious Agent in the Blood Gastroenterology 1979 Apr. 76(4):680-4.

Tabor et al. Inactivation of an Agent of Human Non-A, Non-B Hepatitis by Formalin (unpublished).

*Primary Examiner*—Shep K. Rose
*Attorney, Agent, or Firm*—John S. Roberts

[57] ABSTRACT

This invention relates to a method of inactivating a non-A, non-B hepatitis agent by means of formalin utilized in extended treatment. The range of formalin treatment utilizes a concentration of 1:1,000-1:10,000, preferred 1:1,000, and the duration of treatment is from 24-120 hours at any temperature with a preferred 96 hours (4 days) at 37°±4° C. This formalin-treated or otherwise inactivated agent, or portions of the agent, may be later used to produce a vaccine against non-A, non-B hepatitis.

4 Claims, No Drawings

INACTIVATION OF NON-A, NON-B HEPATITIS AGENT

This invention relates to a method of inactivating a non-A, non-B hepatitis agent by means of formalin utilized in extended treatment. The range of formalin treatment utilizes a concentration of 1:1,000–1:10,000, preferred 1:1,000, and the duration of treatment is from 24–120 hours at any temperature with a preferred 96 hours (4 days) at 37°±4° C. This formalin-treated or otherwise inactivated agent, or portions of the agent, may be later used to produce a vaccine against non-A, non-B hepatitis.

The agent of non-A, non-B hepatitis described here is completely different from the hepatitis A and B viruses. It does not react immunologically with tests for those viruses. Recovery from one agent does not protect against infection by one of the others.

The present application is devoted to the use of formalin. A preferred formalin is an aqueous 37–50% solution of formaldehyde which may contain 15% methyl alcohol (Condensed Chemical Dictionary, 9, 1977, Van Nostrand Reinhold, page 395).

The utility of the present method may additionally include the preparation of a vaccine with or without the addition of a suitable adjuvant.

The suitability of the chimpanzee as an animal model for the evaluation of this invention has been well documented. Chimpanzees and humans are immunologically and biochemically similar. The chimpanzee has been shown to be susceptible to human non-A, non-B hepatitis and to respond with similar enzyme elevations and similar biopsy changes to those of humans with this infection. See Tabor, et al., Lancet and Gastroenterology, below.

Non-A, non-B hepatitis has been shown to be caused by a transmissible agent and the chimpanzee has been shown to be a suitable animal model for the study of this disease as noted above. The agent of this disease may remain present in blood for prolonged periods of time, but immunity to reinfection has been shown to follow recovery from infection in both humans and chimpanzees.

PRIOR ART STATEMENT

Tabor, et al, "Transmission of Non-A, Non-B Hepatitis from Man to Chimpanzee," *The Lancet*, Mar. 4, 1978, pages 463–466.

Tabor, et al, "Acute Non-A, Non-B Hepatitis Prolonged Presence of the Infectious Agent in Blood," Gastroenterology, Vo. 76, No. 4, Apr. 1979, pages 680–684.

Tabor, et al, "Inactivation of an Agent of Human Non-A, Non-B Hepatitis by Formalin," abstract in *Hepatitis Scientific Memorandum*, (H-1723, Mar. 1980).

Related application of Tabor et al, Ser. No. 40,921 filed May 21, 1979, "Detection of Non-A, Non-B Hepatitis."

EXPERIMENTAL

An agent of human non-A, non-B hepatitis was shown to be present in the serum of an experimentally infected chimpanzee by transmission of the disease to five additional chimpanzees by inoculation of 0.1 to 1.0 ml of this serum, including two inoculated subsequent to the present invention. Samples of this serum (0.1 ml each) were incubated with formalin in a final concentration of 1:1,000 at 37° C. for 96 hours. Three colony-born infant chimpanzees were then inoculated with this formalin-treated serum; one received a single intravenous inoculation and two received two subcutaneous inoculations one month apart. A fourth uninoculated chimpanzee served as a control. None developed recognizable non-A, non-B hepatitis during seven months of observation, as judged by normal aminotransferase levels in weekly serum samples, normal liver histology in bi-weekly liver biopsies, and the absence of the non-A, non-B hepatitis associated antigen and antibody in their sera. All four chimpanzees remained susceptible and developed non-A, non-B hepatitis when subsequently challenged with 0.1 ml of untreated serum 31 weeks after the initial inoculations.

Chimpanzees. Four chimpanzees (*Pan troglodytes*), #A-6, #A-8, #A-9, #A-11, born in a U.S. breeding colony were studied. Each was between 13 and 14 months of age and weighed between 6 and 10 kg at the onset of this experiment. From birth to 12 months of age, they had been housed together in a nursery and fed an infant formula; the care and feeding after age 12 months has been described by Barker, et al, *J. Infect. Dis.*, 1973, 127:648–662. There was little likelihood of prior exposure to hepatitis viruses. The only potential sources were their human caretakers and other infant chimpanzees. All were tested monthly and had normal values for serum aspartate aminotransferase (AST) and alanine aminotransferase (ALT). All remained negative for the serologic markers of hepatitis A and B. None had been previously inoculated with any blood or plasma product. The parents of these infant chimpanzees, while not in contact with them after birth, were also monitored at regular intervals for AST and ALT.

Serologic Studies. Beginning four weeks before inoculation and continuing throughout the experiment, serum specimens from the chimpanzees were tested weekly for AST and ALT (ABA-100, Abbott Laboratories, North Chicago, Illinois) (normal, $\leq$40 IU/1), for isocitric dehydrogenase (ICD) by the Sigma method, for HBsAg by radioimmunoassay (RIA) (Austria II, Abbott Laboratories), for antibody to HBsAg (anti-HBs) by RIA (Ausab, Abbott Laboratories), for antibody to hepatitis B core antigen (anti-HBc) by RIA (Corab, Abbott Laboratories), and for an antigen-antibody system shown to be associated with non-A, non-B hepatitis by counterelectrophoresis. Selected serum samples were tested for antibody to HAV (anti-HAV) by RIA (Havab, Abbott Laboratories), for antibody to cytomegalovirus (anti-CMV) by enzyme-linked immunosorbent assay and for antibody to the capsular antigen of the Epstein-Barr virus (anti-EBV) by indirect immunofluorescence.

Liver Biopsies. Liver biopsy specimens were obtained bi-weekly. The chimpanzees were anesthetized with cyclohexylamine, a drug with no known liver toxicity. The specimens, obtained with a 14 gauge Vim-Silverman needle, were stained with hematoxylin and eosin. Coded biopsy specimens were assessed by the criteria of Barker et al, *J. Infect. Dis.*, 127:648–662, 1973, and were considered positive if lymphocytic infiltration of the sinusoids or portal areas together with eosinophilic degeneration or acidophilic bodies were observed.

Inocula and Formalin Treatment. Chimpanzee #930 was infected with an agent of human non-A, non-B hepatitis by experimental inoculation of 0.1 ml of serum from a chronically infected human (Inoculum I) who transmitted this disease to a nurse who injured herself with a broken capillary pipette contaminated with his blood. Four weeks after inoculation and one week after onset of aminotransferase elevations, serum was obtained from chimpanzee #930 and designated Inoculum Ip2w4. All three developed elevated aminotransferase levels and histologic evidence of hepatitis in liver biopsies. Incubation periods ranged from 2 to 5 weeks.

TABLE 1

| | Infectivity of Inoculum Ip2w4 | | | | |
|---|---|---|---|---|---|
| When Inoculated | Recipient Chimpanzee | Inoculum Dilution | Weeks AST, ALT Elevated | Peak ALT (week) | Week Abnormal Liver Biopsy |
| Prior to Experiment | #911 | $10^0$ | 5–14* | 244 IU/1 (8) | 8 |
| | #968 | $10^{-1}$ | 2–11 | 358 IU/1 (10) | 4 |
| | #974 | $10^{-1}$ | 3–15 | 171 IU/1 (13) | 14 |
| Subsequent to Experiment | #A-11 | $10^{-1}$ | 4-present 215 IU/1 (5) | 6 | |
| | #A-52 | $10^{-1}$ | 2-present | 84 IU/1 (2) | 6 |

*Intermittent elevations until week 49.

tained from chimpanzee #930 and designated Inoculum Ip2w4. This serum was distributed in separate vials of one ml, either undiluted or a $10^{-1}$ dilution in fetal bovine serum, and these vials were stored at −70° C.

Five vials, each containing one ml of a $10^{-1}$ dilution of Inoculum Ip2w4, were thawed for formalin treatment. A fresh 1% formalin solution (prepared from Formaldehyde Solution, USP; JT Baker Chemical Co., Phillipsburg, New Jersey) was added to each vial to give final concentration of 1:1,000 formalin. The vials were incubated at 37° C. using mechanical agitation for 96 hours and were stored at 4° C. until inoculation into chimpanzees three days (or 31 days for the second dose) thereafter.

Inoculations, Initial and Challenge. Chimpanzee #A-9 was given a single intravenous inoculation of the contents of one of the formalin-treated vials. Chimpanzees #A-6 and #A-8 were each inoculated subcutaneously with the contents of one of the formalin-treated vials. A second subcutaneous inoculation was given to these two chimpanzees four weeks later. Chimpanzee #A-11 served as an uninoculated control.

Challenge inoculations were conducted thirty-one weeks after the initial inoculations. Each chimpanzee was inoculated intravenously with one ml of a $10^{-1}$ dilution of untreated Inoculum Ip2w4, which had been continuously stored at −70° C.

Results. No evidence of non-A, non-B hepatitis was detected in any of the chimpanzees during seven months of observation following the initial inoculations. AST, ALT, and ICD values remained in or near the preinoculation range for each chimpanzee. No evidence of hepatitis was detected in bi-weekly liver biopsy specimens. No serologic evidence of infection by hepatitis A virus, hepatitis B virus, cytomegalovirus, or Epstein-Barr virus was detected. Weekly serum samples remained negative for the non-A, non-B hepatitis associated antigen and antibody.

The infectivity of the untreated Inoculum Ip2w4 was established by the intravenous inoculation of one ml of either the undiluted inoculum or a $10^{-1}$ dilution in five of five chimpanzees, including two inoculated subsequent to the present experiment. See Table I below. All five developed non-A, non-B hepatitis with incubation periods from inoculation to time of first aminotransferase elevation ranging from two to five weeks. Each chimpanzee developed peak ALT of 84-358 IU/1 between weeks 2 and 13; each chimpanzee developed histologic evidence of acute hepatitis in liver biopsy specimens between weeks 4 and 14.

Challenge inoculations were conducted in chimpanzees #A-6, #A-8, and 190 A-9 31 weeks after initial inoculations, each receiving one ml of a $10^{-1}$ dilution of untreated Inoculum Ip2w4. All three developed elevated aminotransferase levels and histologic evidence of hepatitis in liver biopsies. Incubation periods ranged from 2 to 5 weeks.

DISCUSSION

This experiment relates to the inactivation by formalin of an agent of human non-A, non-B hepatitis. The formalin-treated serum containing an agent of human non-A, non-B hepatitis was administered subcutaneously to two chimpanzees and intravenously to one. The suitability of the subcutaneous route in two of these chimpanzees for evaluating the infectivity of the agent(s) of non-A, non-B hepatitis has been established in humans by Hoofnagle, et al, *Ann. Int. Med.,* 87:14–20, 1977. Parenteral routes other than intravenous have also been shown to be suitable in chimpanzees by Hollinger et al, *Intervirology,* 10:60–68, 1978. All three chimpanzees inoculated with the formalin-treated serum failed to develop recognizable non-A, non-B hepatitis and remained susceptible to non-A, non-B hepatitis when subsequently inoculated with the same volume and dilution of untreated serum. If sufficient material were used to induce an immune response, it is expected that resistance to infection would be produced.

Although the exact infectivity titer of Inoculum Ip2w4 was not determined here, a minimum titer of $\geq 10^{1.5}$ infectious doses per ml was established. Four of four chimpanzees inoculated with one ml of a $10^{-1}$ dilution (Table 1) and three of three chimpanzees challenged with one ml of a $10^{-1}$ solution in this experiment developed non-A, non-B hepatitis.

The agent here has been shown to be responsible for non-A, non-B hepatitis in posttransfusion episodes in different geographic areas of the United States. It is transmissible to humans and chimpanzees and it may be serially passaged in chimpanzees. The agent may remain present in blood for prolonged periods of time, but apparent recovery from active infection results in immunity to reinfection by induction of a protective immune response. The present invention shows that this agent can be inactivated by formalin.

We claim:

1. A method of treating an agent of human non-A, non-B hepatitis virus with formalin at a concentration of 1:1,000–1:10,000 for 24–120 hours to inactivate said agent.

2. The method of claim 1 wherein lack of further infectivity of said agent is demonstrated by inoculation in a human.

3. The method of claim 2 wherein the inoculation is in a chimpanzee.

4. The method of claim 1 wherein formalin is used at a concentration of 1:1,000 for about 96 hours at 37°±4° C.

* * * * *

UNITED STATES PATENT OFFICE
CERTIFICATE OF CORRECTION

Patent No. 4,291,020          Dated September 22, 1981

Inventor(s) Edward Tabor and Robert J. Gerety

It is certified that error appears in the above-identified patent and that said Letters Patent are hereby corrected as shown below:

Column 4, Table 1, the line for Recipient Chimpanzee #A-11 should be as follows:

| Recipient Chimpanzee | Inoculum Dilution | Weeks AST, ALT Elevated | Peak ALT (week) | Week Abnormal Liver Biopsy |
|---|---|---|---|---|
| #A-11 | $10^{-1}$ | 4-present | 215 IU/1 (5) | 6 |

Signed and Sealed this

Twenty-fourth Day of November 1981

[SEAL]

Attest:

GERALD J. MOSSINGHOFF

Attesting Officer     Commissioner of Patents and Trademarks